US012558060B2

(12) United States Patent
Jørgensen et al.

(10) Patent No.: US 12,558,060 B2
(45) Date of Patent: Feb. 24, 2026

(54) ROBOTIC SYSTEM FOR PERFORMING AN ULTRASOUND SCAN

(71) Applicant: ROPCA ApS, Odense M (DK)

(72) Inventors: Johannes Chemnitz Albinus Jørgensen, Odense NV (DK); Thiusius Rajeeth Savarimuthu, Odense SV (DK)

(73) Assignee: ROPCA ApS, Odense M (DK)

( * ) Notice: Subject to any disclaimer, the term of this patent is extended or adjusted under 35 U.S.C. 154(b) by 92 days.

(21) Appl. No.: 18/269,164

(22) PCT Filed: Dec. 20, 2021

(86) PCT No.: PCT/EP2021/086841
§ 371 (c)(1),
(2) Date: Jun. 22, 2023

(87) PCT Pub. No.: WO2022/136294
PCT Pub. Date: Jun. 30, 2022

(65) Prior Publication Data
US 2024/0074729 A1 Mar. 7, 2024

(30) Foreign Application Priority Data

Dec. 22, 2020 (DK) ............................ PA 2020 70866

(51) Int. Cl.
*A61B 8/00* (2006.01)
(52) U.S. Cl.
CPC .......... *A61B 8/4218* (2013.01); *A61B 8/4263* (2013.01); *A61B 8/54* (2013.01)

(58) Field of Classification Search
CPC ..... A61B 34/30; A61B 8/4209; A61B 8/4218; A61B 8/4263; A61B 8/4477; A61B 90/50; A61B 8/145; A61B 8/52; A61B 8/54; G06T 2207/30168; G06T 7/0002; G06V 10/993; G06V 10/98
See application file for complete search history.

(56) References Cited

U.S. PATENT DOCUMENTS

| | | | |
|---|---|---|---|
| 10,470,740 | B2 | 11/2019 | Freudenberger et al. |
| 2007/0205785 | A1 | 9/2007 | Nilsson |
| 2009/0088639 | A1 | 4/2009 | Maschke |
| 2012/0022552 | A1 | 1/2012 | Neff |
| 2012/0271173 | A1 | 10/2012 | Li |
| 2013/0329038 | A1 | 12/2013 | Hager et al. |

(Continued)

FOREIGN PATENT DOCUMENTS

| | | | | |
|---|---|---|---|---|
| CN | 103690191 | A | 4/2014 | |
| CN | 110974299 | A * | 4/2020 | ............. G06N 3/045 |

(Continued)

*Primary Examiner* — Keith M Raymond
*Assistant Examiner* — Milton Truong
(74) *Attorney, Agent, or Firm* — Flaster Greenberg P.C.

(57) ABSTRACT

A robotic system for performing an ultrasound scan on a body part of a patient. The robotic system comprises a positioning device configured to hold and move an ultrasound probe, a sensor configured to obtain position data, and a control unit. The control unit being configured to generate first movement instructions based on received position data, and second movement instructions using a machine learning data architecture trained to evaluate an ultrasound image of the body part.

14 Claims, 3 Drawing Sheets

(56) References Cited

U.S. PATENT DOCUMENTS

| 2016/0135782 A1 | 5/2016 | Chen et al. |
| 2017/0011185 A1 | 1/2017 | Schweizer |
| 2017/0143303 A1* | 5/2017 | Chen ..................... A61B 8/488 |
| 2017/0181725 A1 | 6/2017 | Han et al. |
| 2017/0215844 A1 | 8/2017 | Han et al. |
| 2017/0252002 A1* | 9/2017 | Mine ................... A61B 8/4218 |
| 2018/0028142 A1 | 2/2018 | Bhatia et al. |
| 2018/0250087 A1 | 9/2018 | Grasser et al. |
| 2018/0317881 A1* | 11/2018 | Astigarraga ......... A61B 8/0891 |
| 2018/0344284 A1 | 12/2018 | Freudenberger et al. |
| 2019/0147305 A1* | 5/2019 | Lu ....................... G06F 18/2413 |
| | | 382/157 |
| 2019/0320878 A1* | 10/2019 | Duindam .................. G06T 7/30 |
| 2019/0392582 A1 | 12/2019 | Gemmel et al. |
| 2020/0029941 A1 | 1/2020 | Avendi et al. |
| 2020/0069284 A1 | 3/2020 | Kobayashi et al. |
| 2020/0069292 A1* | 3/2020 | Abolmaesumi ...... A61B 8/5207 |
| 2020/0069797 A1 | 3/2020 | Dean et al. |
| 2020/0098106 A1* | 3/2020 | Moriyasu ............... G16H 30/40 |
| 2020/0194117 A1 | 6/2020 | Krieger et al. |
| 2020/0281667 A1 | 9/2020 | Blondel et al. |
| 2020/0297308 A1 | 9/2020 | Kobayashi et al. |
| 2020/0297318 A1 | 9/2020 | Srinivasa Naidu et al. |

FOREIGN PATENT DOCUMENTS

| CN | 110974299 A1 | 4/2020 |
| JP | 2017159027 A | 9/2017 |
| WO | 2018146682 A1 | 8/2018 |
| WO | 2019175129 A1 | 9/2019 |

* cited by examiner

ROBOTIC SYSTEM FOR PERFORMING AN ULTRASOUND SCAN

CROSS-REFERENCE TO RELATED APPLICATIONS

This application is the 371 National Stage of International Application No. PCT/EP2021/086841, filed Dec. 20, 2021, which claims priority to Danish Application No. PA 2020 70866, filed Dec. 22, 2020, the disclosures of which are incorporated herein by reference in their entireties.

TECHNICAL FIELD

The present invention relates to a robotic system for performing an ultrasound scan on a body part of a patient.

BACKGROUND ART

Ultrasound scans are widely employed within the medical world, for example as a diagnostic tool when scanning foetuses, when diagnosing hand or foot injuries, or diseases such as rheumatoid arthritis or gout.

Most ultrasound scan are carried out by a trained medical professional. However, even the most trained ultrasound technicians experience difficulties in performing ultrasound scans in a consistent and efficient manner. Furthermore, only a limited amount of trained medical professionals is out there, thus the wait time for being examined by one can in some cases be very long. The long wait time may lead to a disease or injury worsening before being examined.

To overcome some of the above problems robotic ultrasound systems have been developed. Robotic ultrasound systems may obtain ultrasound scans in an efficient and consistent manner which may lead to lower wait times for patients and improved ultrasound scans.

An example of such a system is seen in U.S. Pat. No. 10,470,740 B2. U.S. Pat. No. 10,470,740 B2 discloses a method for moving a robot arm for an ultrasound examination, an ultrasound probe being attached to the robot arm. An associated ultrasound system is also disclosed. In an embodiment, the method includes providing a trained artificial neural network recording a medical issue; determining a motion dataset containing a motion sequence of the robot arm by applying the trained artificial neural network to the medical issue; transferring the motion dataset to a controller of the robot arm, and moving the robot arm in accordance with the motion sequence of the motion dataset.

However, these systems still suffer from drawbacks. The robotic systems still struggle to achieve high quality ultrasound images.

SUMMARY OF THE INVENTION

It is an object of the present invention to provide an improved robotic system.

In a first aspect of the invention, this and further objects are achieved by a robotic system for performing an ultrasound scan on a body part of a patient using an ultrasound imaging system comprising an ultrasound probe, the robotic system comprising a positioning device configured to hold and move an ultrasound probe to obtain the ultrasound scan of the body part, a sensor configured to obtain position data on the body part, and a control unit configured to receive position data from the sensor, to generate, based on the received position data, a first movement instruction for the positioning device for moving the ultrasound probe to obtain a first ultrasound image of the body part, to receive from the ultrasound imaging system the first ultrasound image of the body part, and to evaluate the received first ultrasound image using a machine learning data architecture trained to evaluate an ultrasound image of the body part.

Consequently, a robotic system for performing an ultrasound scan on a body part is provided which can achieve high quality ultrasound images of patients without the need for highly trained personnel. By firstly obtaining a first ultrasound image and then evaluating these it is possible to obtain a high-quality ultrasound image is achieved. Furthermore, since the evaluation of the ultrasound images is automated, it allows the ultrasound scan to be carried out quickly and allows for quick identification of the best ultrasound images.

The body part may be a hand, a foot, an arm, a leg, a torso, or other body parts of a patient undergoing the ultrasound scan.

The ultrasound imaging system may be any system where the ultrasound probe is configured to emit and detect ultrasound waves. The ultrasound imaging system may further comprise an ultrasound processing unit operationally connected to the ultrasound probe. The ultrasound processing unit is a unit comprising any circuit and/or device suitably adapted to perform the functions described herein. The ultrasound processing unit may comprise general purpose or proprietary programmable microprocessors, such as Digital Signal Processors (DSP), Application Specific Integrated Circuits (ASIC), Programmable Logic Arrays (PLA), Field Programmable Gate Arrays (FPGA), special-purpose electronic circuits, etc., or a combination thereof. The ultrasound processing unit may control operation of the ultrasound probe, i.e. the emittance of ultrasound from the ultrasound probe. The ultrasound processing unit may be communicatively connected to the ultrasound probe. The ultrasound processing unit may be configured to receive data from the ultrasound probe indicative of detected ultrasound waves. The ultrasound processing unit may be configured to generate ultrasound images based on data indicative of detected ultrasound waves received from the ultrasound probe. The ultrasound processing unit may be communicatively connected to the control unit to receive signals from the control unit and/or transmit signals to the control unit. The ultrasound processing unit may be configured to transmit generated ultrasound images to the control unit. The control unit may transmit control signals to the ultrasound imaging system to control operation of the ultrasound imaging system. The control signals may control an ultrasound mode used for obtaining ultrasound images. The control signal may control parameters of the ultrasound imaging system, e.g. intensity, frequency, and/or modulation of ultrasound waves emitted by the ultrasound imaging system.

The control unit is a unit comprising any circuit and/or device suitably adapted to perform the functions described herein. The control unit may comprise general purpose or proprietary programmable microprocessors, such as Digital Signal Processors (DSP), Application Specific Integrated Circuits (ASIC), Programmable Logic Arrays (PLA), Field Programmable Gate Arrays (FPGA), special-purpose electronic circuits, etc., or a combination thereof. The control unit may comprise a transmitter, a receiver, and/or a transceiver for transmitting and receiving signals. The control unit may comprise a data storage for storing the first ultrasound image and/or the second ultrasound image. The robotic system may comprise a display, the display may be operationally connected to the control unit. The control unit may retrieve an ultrasound image from the data storage and display the ultrasound image on the display.

The control unit is communicatively connected to the sensor. The sensor may be a 2D camera and/or a 3D camera, and/or a LIDAR sensor.

The position data may comprise data regarding a position of the body part relative to the positioning device. The position data may comprise data regarding an orientation of the body part relative to the positioning device. The position data may indicate the position and/or orientation of the body part in system coordinates, wherein the position and/or orientation of the positioning device is known within the system coordinates. The sensor may be configured to continuously obtain position data during the scan, thus allowing the control unit to take into account movement of the body part during the scan.

The first movement instruction generated may instruct the positioning device for moving the ultrasound probe to obtain a first ultrasound image of the body part at a first position and orientation. The first movement instruction generated may instruct the positioning device for moving the ultrasound probe to obtain a plurality of first ultrasound images of the body part at a plurality of first positions and orientations. The first movement instruction may be generated together with control signals for the ultrasound imaging system for when and how to obtain ultrasound images, e.g. the control unit may generate the control signals in response to determining, based on the first movement instruction, when a desired position has been reached.

The received first ultrasound image may be a single first ultrasound image or it may be a plurality of first ultrasound images. The plurality of first ultrasound images may be obtained by a sweeping scan, wherein the ultrasound probe is continuously moved while obtaining the plurality of first ultrasound images. Alternatively, the ultrasound probe may be kept fixed at different positions while obtaining the plurality of first ultrasound images. The control unit may be configured to continuously receive ultrasound images obtained by the ultrasound imaging system. The ultrasound imaging system may transmit obtained ultrasound images to the control unit continuously as the ultrasound images are obtained.

Evaluating the first ultrasound image may comprise assigning a score to the first ultrasound image. Evaluating the first ultrasound image may comprise determining anatomical features in the first ultrasound image, e.g. a location of a joint in the first ultrasound image may be determined. Evaluating the first ultrasound image may comprise determining an image quality of the first ultrasound image. Evaluating the first ultrasound image may comprise determining an instruction for the positioning device to obtain a higher quality second ultrasound image.

The machine learning data architecture may be trained by evaluating a training data set comprising plurality of training ultrasound images. The plurality of training ultrasound images may be ultrasound images obtained by medical professionals. The plurality of training ultrasound images may be ultrasound images previously obtained by the robotic system. Each of the training ultrasound images may have a score attached to them to indicate the quality of the training ultrasound images indicating the quality of the ultrasound image. The score may be assigned by a medical professional, i.e. the machine learning data architecture may be a supervised learning model. The quality may indicate the ability of the ultrasound image for being used for diagnostic purposes. The medical professional may use his/her experience when assigning scores. The score may be a binary score e.g. bad/good, or a score on a scale e.g. from 0 to 100. The machine learning data architecture may be trained for different anatomical features, e.g. for evaluating different joints in hands and feet. Thus, for each joint the machine learning data architecture may have been provided with a specific training data set. The machine learning data architecture may be an artificial neural network such as a deep structured learning architecture. If the robotic system is to be used for scanning joints, the machine learning data architecture may be trained to identify and evaluate an image quality of a joint capsule and bones surrounding the joint capsule.

In an embodiment the control unit is further configured to:
generate, based on the evaluated the first ultrasound image, second movement instructions for the positioning device for moving the ultrasound probe to obtain a second ultrasound images of the body part.

Consequently, the robotic system employs an iterative approach to obtain ultrasound images, thus allowing for confirmation of the quality of the first ultrasound images. The second movement instruction generated may instruct the positioning device for moving the ultrasound probe to obtain a second ultrasound image of the body part at a second position and orientation. The second movement instruction generated may instruct the positioning device for moving the ultrasound probe to obtain a plurality of second ultrasound images of the body part at a plurality of second positions and orientations. Alternatively, the second movement instruction generated may instruct the positioning device to stay at its current position. The second movement instruction may be generated in response to evaluating the first ultrasound image to be of sufficient quality. The second movement instruction may then be an instruction prompting the positioning device to revisit the location in which the first ultrasound image was acquired. Alternatively, if the first ultrasound image is determined to be of insufficient quality the second movement instruction may prompt the positioning device to move the ultrasound probe to obtain a second ultrasound images of the body part at a different location than the location where the first ultrasound image was acquired. If the first ultrasound image is evaluated to comprise one or more flaws resulting in insufficient quality, the controller may generate a second movement instruction for overcoming the one or more flaws and achieving a second ultrasound image of sufficient quality. For example, the controller using the machine learning data architecture evaluates the first ultrasound image to be skewed to the left or right, or to be out of focus then the second movement instruction may be generated to compensate for the evaluated flaws, e.g. by moving the ultrasound probe to the right or to the left, or to change an orientation of the ultrasound probe to improve the focus.

In some embodiments, the first movement instruction for the positioning device is for moving the ultrasound probe to obtain a plurality first ultrasound image of the body part at a plurality of positions.

In some embodiments, the second movement instructions are for the positioning device to move the ultrasound probe to a position where the first ultrasound image were obtained and to obtain the second ultrasound image of the body part at that position. Where a plurality of first ultrasound images are obtained, potentially at a plurality of positions, the second movement instruction may be for the positioning device to move the ultrasound probe to a position, at which at least one of the first ultrasound image were obtained and to obtain the second ultrasound image of the body part at that position.

The second movement instruction may be generated in response to obtaining a first ultrasound image or a plurality of first ultrasound images at a first position or plurality of first positions, respectively. The first ultrasound image or plurality of first ultrasound images may comprise a first level of detail.

The control unit may further be configured to determine an image quality of the received first ultrasound image(s). An image quality of an ultrasound image may comprise and/or be a quality score. Where a score is determined by a using the machine-learning data architecture, the quality score may be and/or comprise the score. A image quality of an ultrasound image may be based on one or more of anatomical features seen in the first ultrasound image and/or orientation and placement of the ultrasound probe in relation to the body part which is scanned.

The control unit may compare the determined image quality of the first ultrasound image(s). The control unit may compare a respective determined quality of a plurality of first ultrasound images and/or compare an image quality of a first ultrasound image with an image quality threshold. An image quality threshold may be a predetermined image quality threshold or an adaptive image quality threshold, potentially determined by the control unit.

Where a plurality of first images are obtained, the control unit may determine which first ultrasound image of the plurality of first ultrasound images has a highest image quality, potentially based on a comparison of determined image qualities for the plurality of images. Additionally or alternatively, the control unit may determine if an image quality of an ultrasound image, such as the determined highest image quality, meets a required image quality threshold. Potentially, the second movement instruction may be to revisit the position, at which the first ultrasound image having the highest determined image quality was obtained. The control unit may generate second movement instructions for the positioning device for moving the ultrasound probe to obtain a second ultrasound image or plurality of second ultrasound images at the revisited position. The second ultrasound image(s) may have a second level of detail.

In this and other embodiments, the second level of detail may be higher than the first level of detail.

Alternatively or additionally, the second movement instruction may be generated in response to a prediction by the control unit, of a desired second position for obtaining a second ultrasound image or plurality of second ultrasound images. The prediction may be based on the evaluation of the first ultrasound image(s) obtained at the first position or plurality of first positions. The evaluation of the first ultrasound image(s) may include determining an image quality of the first ultrasound image(s). In some embodiments, the control unit may, based on the evaluation, predict a subsequent position, such as a subsequent first position, for obtaining a subsequent first ultrasound image or plurality of subsequent first ultrasound images. The predicted subsequent position may be a position, at which the control unit estimates that a first and/or second ultrasound image has a higher image quality than that of the first image(s). The control unit may, based on the predicted subsequent first position, instruct the positioning device to move the ultrasound probe to the subsequent position and obtain a subsequent first ultrasound image or plurality of subsequent first ultrasound images.

The control unit may receive the subsequent first ultrasound image(s) and make a subsequent evaluation. Based on the subsequent evaluation of the subsequent first ultrasound image(s) the control unit may predict a need to obtain further subsequent first ultrasound image(s) at a subsequent and/or already visited position(s). The control unit may continue to receive the subsequent first ultrasound image(s) and make subsequent evaluations and predictions until a subsequent position is reached where a subsequent first ultrasound image(s) is obtained, having a determined image quality above a determined or predetermined threshold quality. In response to receiving the subsequent first ultrasound image(s) having a determined image quality meeting a determined or preset threshold, the control unit may instruct the ultrasound probe to obtain a second ultrasound image or plurality of second ultrasound images having a second level of detail.

In an embodiment the positioning device comprises a robotic arm.

By providing a robotic arm a high degree of freedom in the movement of the ultrasound probe is achieved. The positioning device may be any articulated arm configured to hold an ultrasound probe and move the ultrasound probe. The robotic arm may comprise a plurality of joints linked together. The robotic arm may be capable of movement in three dimensions. The articulated arm may comprise a holder for holding the ultrasound probe. The holder may be integrated into an end piece of the robotic arm. The end piece may be the last joint of the robotic arm. Alternatively, the holder may be connectable to the end piece of the robotic arm. The robotic arm may be provided with a receiver, a transmitter, and/or a transceiver for receiving and transmitting signals either through a wired or a wireless connection. The robotic arm may further comprise a robotic arm processing device. The robotic arm processing device is a device comprising any circuit and/or device suitably adapted to perform the functions described herein. The robotic arm processing device may comprise general purpose or proprietary programmable microprocessors, such as Digital Signal Processors (DSP), Application Specific Integrated Circuits (ASIC), Programmable Logic Arrays (PLA), Field Programmable Gate Arrays (FPGA), special-purpose electronic circuits, etc., or a combination thereof. The robotic arm may be provided with an arm sensor. The arm sensor may be for collecting data regarding movement of the robotic arm, such an arm sensor could be a gyroscope or an accelerometer. The arm sensor may be a force sensor configured to detect a force exerted by the robotic arm on a patient undergoing the automatic scan. The arm sensor may be communicatively connected to the control unit to transmit detected data to the control unit. The robotic arm processing device may receive signal from the control unit and adjust movement of the robotic arm based on the data received. Data collected by sensors provided with the robotic arm may be transmitted to the control unit. The control unit may use received sensor data in controlling movement of the robotic arm.

The positioning device may alternatively be a rail system configured to hold the ultrasound probe and move the ultrasound probe to obtain the ultrasound scan. The rail system may comprise an ultrasound probe holder connected to a rail of the rail system. The rail system may comprise two rails angled in relation to each, thus allowing movement within a plane defined by the two rails. The two rails may be perpendicular to each other. The rail system may comprise three rails angled in relation to each, thus allowing movement within a 3D space defined by the three rails. The three rails may be perpendicular to each other.

In an embodiment the sensor comprises a 2D and/or a 3D camera configured to obtain image data on the body part.

In some embodiment the robotic system comprises a sensor assembly comprising a plurality of 2D sensors and/or a plurality of 3D sensors. In some embodiments the 3D sensor is composed of at least two 2D sensors. For example, the 3D sensor may consist of two 2D cameras configured to obtain image data of the body part at different angles. The image data obtained by the two cameras may be transmitted and processed by the control unit to obtain 3D data regarding the body part supported by the support surface.

The 2D sensor and/or 3D sensor may be configured for obtaining depth data of the body part supported by the support surface, which may be used by the control unit to create a depth map of the body. The control unit may use the depth map in controlling movement of the positioning device.

The 2D sensor and/or 3D sensor may be configured for obtaining data regarding a position and/or orientation of the ultrasound probe. The 2D sensor and/or 3D sensor may be configured for obtaining data regarding a position and/or orientation of a surface of the body part. The position and/or orientation data may be transmitted to the control unit. The control unit may use the received position and/or orientation data in controlling movement of the positioning device.

The data obtained by the 2D sensor and/or 3D sensor may be processed by the control unit to classify a body part to be scanned, e.g. classifying whether a left or a right hand is being scanned or is to be scanned.

The 2D sensor and/or 3D may comprise a receiver, a transmitter, or a transceiver for sending and receiving signals. The 2D sensor and/or 3D sensor may be communicatively connectable to the control unit.

In an embodiment the first movement instruction comprises a first ultrasound probe position and a first associated ultrasound probe orientation for moving the ultrasound probe to obtain the first ultrasound image of the body part.

Consequently, by providing both the first ultrasound probe position and the first associated ultrasound probe orientation a high degree of precision is obtained, thus facilitating obtaining a high quality first ultrasound image.

The first ultrasound probe position and the first associated ultrasound probe orientation may be defined as coordinates in system coordinates, wherein a position and/or orientation of the positioning device is known within the system coordinates.

The first movement instruction may comprise a plurality of first ultrasound probe positions and a plurality of first associated ultrasound probe orientations for moving the ultrasound probe to obtain a plurality of first ultrasound images of the body part.

The first movement instruction may define a scanning path for moving the ultrasound probe to obtain a plurality of first ultrasound images of the body part along the scanning path. The plurality of first ultrasound images may be obtained while continuously moving the ultrasound probe along the scanning path, or by intermittently stopping movement of the ultrasound probe along the scanning path. The scanning path may form a continuous line or consists of several interrupted scanning segments. The ultrasound imaging system may obtain a plurality of first ultrasound images along the scanning path. The ultrasound imaging system may obtain first ultrasound images in discrete points point along the scanning path. The control unit may be configured to evaluate the plurality of first ultrasound images while the ultrasound probe is being moved along the scanning path. The control unit may be configured to generate the second movement instruction while the ultrasound probe is being moved along the scanning path. The first movement instructions may be generated without input from the ultrasound imaging system.

In an embodiment the control unit is further configured to:
  determine, based on the received position data, a target area on the body part, and wherein the first movement instruction is for moving the ultrasound probe within the target area to obtain the first ultrasound image of the body part.

By determining target areas, the robotic system does not need to scan the whole of the body part instead the robotic system may be focused on the target area, consequently, the speed and efficiency of the robotic system is increased.

A target area may be any area on the body part comprising an area of interest in the ultrasound scan. For example, if the ultrasound scan is to be used for scanning joints, the target area may be an area covering one or more joints of a patient. In some embodiments control unit is configured to determine a plurality of target areas of the body part, and wherein the first movement instruction is for moving the ultrasound probe within the plurality of target areas to obtain a plurality of first ultrasound images of the body part. The plurality of target areas may cover a plurality of areas of interest, e.g. for hand or a foot the plurality of target areas may cover a plurality of joints on the hand or the foot. The control unit may be configured to identify areas of interest on a body part, based on the received position data. The control unit may be configured to determine the position and orientation of one or more surfaces of the target area on the body part and wherein the position and orientation of one or more surfaces is used to generate the first movement instructions. As an example, if the target area is a specific joint of a finger, the control unit may be configured to process the position data to generate the first movement instructions by firstly determine the location of the specific joint in system coordinates, and secondly the orientations and locations in system coordinates of the skin surfaces at the specific joint and in vicinity of the specific joint. The target area may be identified using a vision algorithm. The vision algorithm may receive the received position data as input. The vision algorithm may return a point of interest as an output of the vision algorithm, e.g. the vision algorithm may identify the center point of a joint. The control unit may determine the target area based on the point of interest. The control unit may transpose a predefined scanning path on the point of interest, e.g. a spiral starting and spiraling out from the point of interest. The control unit may adapt the predefined scanning path to the curvature of skin when transposing the predefined scanning path. The predefined scanning path may define the target area. The vision algorithm may be a machine learning data architecture trained to identify one or more target areas based on the position data. The machine learning data architecture may be trained using a training data set comprising a plurality of position data sets e.g. 2D or 3D images. For each position data set an operator may have identified the target area. As an example, if the target area is a specific joint and the position data is a 3D image, an operator may have identified the location of the specific joint in each 3D image of the training data set. In an embodiment the first movement instruction defines a scanning path comprising a plurality of first ultrasound probe positions and a plurality of first ultrasound probe orientations for moving the ultrasound probe within the target area to obtain a plurality of first ultrasound images of the body part.

The scanning path may fully cover the target area. For example, if the target area is a specific joint the scanning path may be formed as a spiral starting from the center of the joint. The scanning path may be adapted to the curvature of the skin in the target area. The curvature of the skin may be found using the position data e.g. 3D image. If the control unit has determined a plurality of target areas, the scanning path may be a segmented scanning path with one or more segments for each of the plurality of target areas.

In an embodiment the control unit is further configured to: determine if a contact pressure of the ultrasound probe contacting the body part exceeds a contact pressure threshold, wherein if the contact pressure threshold is exceeded the ultrasound scanned is stopped or the ultrasound probe is moved away from the body part.

Consequently, a collaborative robotic system is provided which hinders and prevents the robotic system from harming a patient and/or a user of the robotic system.

The control unit may be communicatively connected to a force sensor configured to measure a contact force between the ultrasound probe and the body part. The force sensor may be connected to the ultrasound probe and/or the positioning device.

In an embodiment the control unit is further configured to: assign a first score to the first ultrasound image using the machine learning data architecture trained to evaluate an ultrasound image of the body part.

Consequently, the first ultrasound image is easier to quantify, thus easing handling of the ultrasound images for the control unit leading to lower requirements for processing power.

The first score assigned may be indicative of an image quality of ultrasound image. The first score assigned may be indicative of an image quality of an anatomical feature on the ultrasound image.

In an embodiment the control unit is further configured to: based on the first score, sort the first ultrasound image into a first group or a second group.

Consequently, the ultrasound images are sorted easing the retrieval of the needed ultrasound images for the control unit. The sorting of the ultrasound images may also ease retrieval of the ultrasound images for medical personnel.

The sorting may be done based on a quality threshold, wherein ultrasound images with a first score above the quality threshold is sorted into the first group, and ultrasound images with a first score below the quality threshold is sorted into the second group.

The quality threshold may be a fixed value. Different anatomical features may have different quality thresholds, e.g. the joint of a thumb may have a different quality threshold value from the joint of a pinky. The quality threshold may be a dynamic value, wherein if a plurality of first ultrasound images is obtained the quality threshold may be set based on the score of the plurality of first ultrasound images, e.g. if 20 first ultrasound images are obtained, the quality threshold may be set as a value in-between the $10^{th}$ and $11^{th}$ highest scores of the 20 first ultrasound images.

In embodiments where a plurality of target areas is determined then each target area may be associated with their own first and second group. Each of the associated first and second group is associated with a quality threshold. The different quality thresholds may differ from each other or have the same value.

The first group may have a maximum size. The first group may have a maximum size of 1-20 first ultrasound images, preferably 5-15 ultrasound images. If the first group has reached the maximum size a new first ultrasound image assigned a first score over the quality threshold may be com-pared to the first ultrasound image with the lowest assigned first score in the first group, if the first score assigned the new first ultrasound exceed the first score of the first ultrasound image with the lowest assigned first score, the new first ultrasound image is sorted into the first group and the first ultrasound image with the lowest assigned first score in the first group is sorted into the second group, if the first score assigned the new first ultrasound image does not exceed the first score of the first ultrasound image with the lowest assigned first score, the new first ultrasound image is sorted into the second group. Alternatively, the number of first sorted first ultrasound images with an assigned first score exceeding the quality threshold and corresponding to the maximum size are sorted into the first group, while the other first ultrasound images are sorted into the second group.

In an embodiment the control unit is further configured to: determine a first acquiring position and/or a first acquiring orientation, wherein the first acquiring position and/or the first acquiring orientation corresponds to a position and/or an orientation of the ultrasound probe and/or the positioning device when the first ultrasound image of the body part was obtained.

The control unit may determine the first acquiring position and/or the first acquiring orientation based on the first movement instruction.

In an embodiment, if the first ultrasound image is sorted in the first group, the second movement instruction comprises a first acquiring position and/or a first acquiring orientation of the first ultrasound image.

Consequently, the positioning device can move the ultrasound probe back to a position and/or an orientation, based on the scores assigned the ultrasound images. This is especially important for assuring that the second ultrasound image is of a high quality. The first acquiring position and/or the first acquiring orientation corresponds to a position and/or an orientation of the ultrasound probe and/or the positioning device when the first ultrasound image of the body part was obtained.

In an embodiment the controller is further configured to: receive from the ultrasound imaging system a second ultrasound image of the body part.

The received second ultrasound image may be a single second ultrasound image or it may be a plurality of second ultrasound images. The second ultrasound image may be an ultrasound image obtained in the same ultrasound mode as the first ultrasound image or in a different ultrasound mode than the first ultrasound image. In an embodiment the first ultrasound image comprises a first level of detail, wherein the second ultrasound image comprise a second level of detail, and wherein the second level of detail is higher than the first level of detail.

Consequently, the first ultrasound image may be obtained via a fast scanning method such as a b-mode ultrasound scan, and the second ultrasound image may be obtained via a slower and more complex scanning method such as a Doppler ultrasound scan e.g. power Doppler, color Doppler, and/or vector Doppler. The control unit may generate control signals for the ultrasound imaging system to obtain the first ultrasound image with a first level of detail and the second ultrasound image with a second level of detail, e.g. by switching ultrasound mode. Alternatively, the first ultrasound images may be obtained via a sweeping ultrasound scan along a scanning path, wherein the ultrasound probe is continuously moving, while the second ultrasound images may be obtained via intermittent ultrasound scans along the scanning path, wherein the ultrasound probe is fixed at discrete points along the scanning scan to obtain the second ultrasound images. If a plurality of first and second ultrasound images are obtained, the first ultrasound image may be used for quickly scanning a large area and determining where areas of interest may be, the second ultrasound images may verify the findings of the first ultrasound images and produce higher quality images of the areas of interest. The level of detail may be defined as an amount of noise in the ultrasound images, wherein a lower degree of noise results in a higher level of detail, and/or the level of detail may be defined as an image quality of the ultrasound images.

In an embodiment the control unit is further configured to:

assign a second score to the second ultrasound image using the machine learning data architecture trained to evaluate an ultrasound image of the body part.

Consequently, the second ultrasound image is easier to quantify, thus easing handling of the ultrasound images for the control unit leading to lower requirements for processing power.

The second score assigned may be indicative of an image quality of ultrasound image. The second score assigned may be indicative of an image quality of an anatomical feature on the ultrasound image.

In an embodiment the control unit is further configured to:

based on the second score, sort the ultrasound image into a third group or a fourth group.

The sorting may be done based on a quality threshold, wherein ultrasound images with a second score above the quality threshold is sorted into the third group, and ultrasound images with a second score below the quality threshold is sorted into the fourth group.

Consequently, the ultrasound images are sorted easing the retrieval of the needed ultrasound images for the control unit. The sorting of the ultrasound images may also ease retrieval of the ultrasound images for medical personnel.

In an embodiment the control unit is further configured to:

if the third group is empty after sorting the second ultrasound image, repeat the ultrasound scan on the body part.

Consequently, the scan may repeat itself to achieve a second ultrasound image of sufficient quality, i.e. a second ultrasound image which is sorted into the third group.

In an embodiment the control unit is further configured to:

if the second ultrasound image is sorted into the third group, generate an ultrasound control signal for the ultrasound imaging system to obtain a third ultrasound image, wherein the third ultrasound image comprises a third level of detail, and wherein the third level of detail is higher than the first level of detail and the second level of detail.

The ultrasound control signal may prompt the ultrasound imaging system to switch ultrasound mode to obtain a third level of detail higher than the first level of detail and the second level of detail.

The control unit may be configured to generate the ultrasound control signal to obtain the third ultrasound image of the body part at a second acquiring positing and a second acquiring orientation. The second acquiring position and/or the second acquiring orientation corresponds to a position and/or an orientation of the ultrasound probe and/or the positioning device where the second ultrasound image of the body part was obtained.

The control unit may be configured to generate the ultrasound control signal as soon as a single second ultrasound image is sorted into the third group. Consequently, allowing for the third ultrasound image to be taken at the same position and/or orientation as the second ultrasound image. The second movement instruction may instruct the positioning device to keep still for a period of time at a position and/or an orientation where a second ultrasound image is to be obtained, where the period of time is long enough to obtain the second ultrasound image and the third ultrasound image.

Consequently, an iterative approach is further facilitated for obtaining high quality ultrasound images. For example, the first ultrasound image may be obtained via a fast scanning method such as a b-mode, wherein the ultrasound probe is continuously moving, the second ultrasound image may be obtained via a b-mode scan, wherein the ultrasound probe is fixed while scanning, and the third ultrasound image may be obtained via a Doppler ultrasound scan e.g. power Doppler, color Doppler, and/or vector Doppler, wherein the ultrasound prove is fixed. Consequently, if a plurality of first and second ultrasound images are obtained, the first ultrasound image may be used for quickly scanning a large area and determining where areas of interest may be, the second ultrasound images may quickly verify the findings of the first ultrasound images, and lastly the third ultrasound images are obtained to achieve high quality ultrasound images of verified areas of interest.

In some embodiments the ultrasound scan is stopped when the third ultrasound image is obtained.

It is noted that the invention relates to all possible combinations of features recited in the claims. Other objectives, features, and advantages of the present inventive concept will appear from the following detailed disclosure, from the attached claims as well as from the drawings. A feature described in relation to one of the aspects may also be incorporated in the other aspect, and the advantage of the feature is applicable to all aspects in which it is incorporated.

BRIEF DESCRIPTION OF DRAWINGS

In the following description embodiments of the invention will be described with reference to the schematic drawings, in which.

DETAILED DESCRIPTION

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided for thoroughness and completeness.

Figure 1:
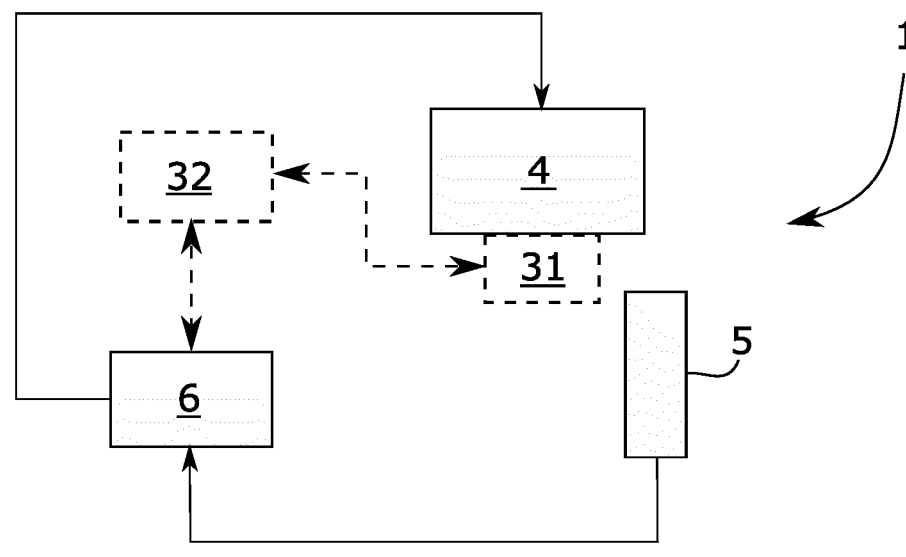
FIG. 1 shows a block diagram of a robotic system 1 according to an embodiment of the invention.

Referring initially to FIG. 1, depicting a block diagram of a robotic system 1 according to an embodiment of the invention. The robotic system 1 being configured for performing an ultrasound scan on a body part of a patient. To carry out the ultrasound scan the robotic system 1 is provided with a positioning device 4. The positioning device 4 is configured to hold an ultrasound probe 31 and move the ultrasound probe 31 to obtain the ultrasound scan of the body part.

The ultrasound probe 31 is part of an ultrasound imaging system which is communicatively and operationally connectable to the robotic system 1. The ultrasound probe 31 is operationally connected to an ultrasound processing unit 32. The ultrasound processing unit 32 is part of the ultrasound imaging system. The ultrasound processing unit 32 is configured to receive data from the ultrasound probe 31 indicative of detected ultrasound waves, and to generate ultrasound images based on data indicative of detected ultrasound waves received from the ultrasound probe 31. The ultrasound processing unit 32 controls operation of the ultrasound probe, e.g. when to emit ultrasound waves. The ultrasound processing unit 32 is communicatively connected to a control unit 6 of the robotic system 1. The ultrasound processing unit 32 being configured to transmit generated ultrasound images to the control unit 6. The ultrasound processing unit 32 is communicatively connected to the control unit 6 to receive control signals from the control unit 6 to control operation of the ultrasound probe 31. Alternatively, the control unit 6 may be directly connected to the ultrasound probe 31 to transmit control signals directly to the ultrasound probe 31.

The control unit 6 is communicatively connected to the positioning device 4, thus allowing the control unit 6 to transmit movement instructions to the positioning device 4 for controlling movement of the positioning device 4. The control unit 6 is further communicatively connected to a sensor 5 to receive position data from the sensor 5. The sensor may be a 2D and/or a 3D camera configured to obtain image data on the body part.

Figure 2:
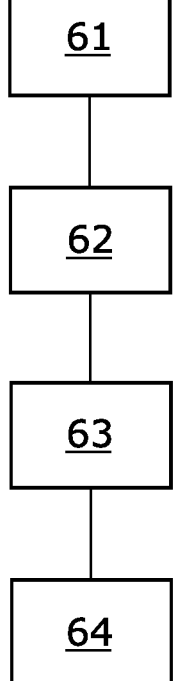
FIG. 2 shows a flow diagram for performing an ultrasound scan according to an embodiment of the invention.

Referring to FIG. 2 showing a flow diagram for performing an ultrasound scan according to an embodiment of the invention. Initially the control unit 6 receives 61 position data from the sensor 5. The position data may be received over a wired and/or a wireless connection. The position data comprising information regarding a position and/or an orientation of a body part of a patient. Based on the received position data, the control unit 6 generates 62, a first movement instruction for the positioning device 4 for moving the ultrasound probe 31 to obtain a first ultrasound image of the body part. The first movement instruction comprising a first position and/or a first orientation for moving the positioning device 4 to allow the ultrasound probe 31 to scan the body part at the first position and/or the first orientation. The first movement instruction may be transmitted to the positioning device 4 via a wired or a wireless connection. The control unit 6 receives 63 from the ultrasound imaging system the first ultrasound image of the body part. The first ultrasound image may be received over a wired and/or a wireless connection. The control unit 6 evaluates 64 the received first ultrasound image using a machine learning data architecture trained to evaluate an ultrasound image of the body part.

Figure 3:
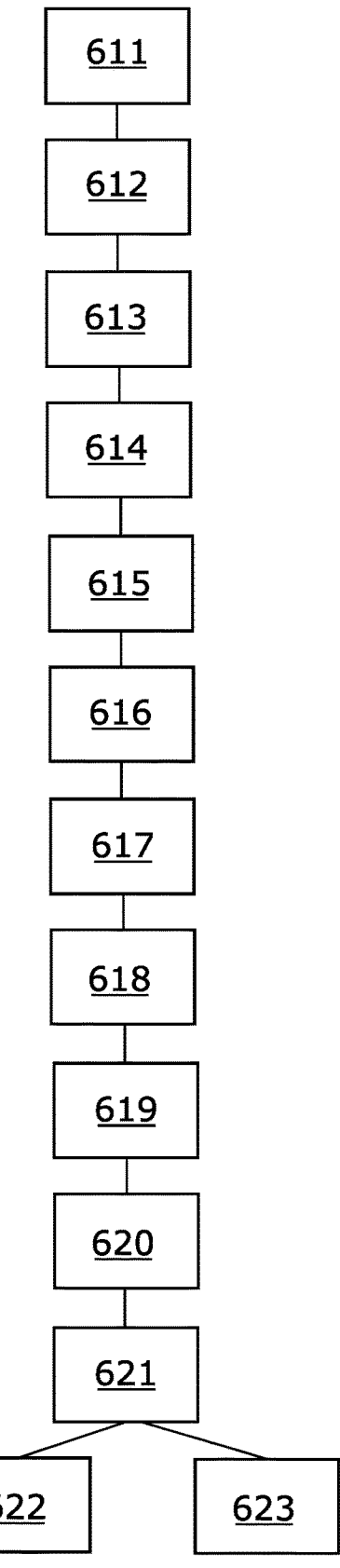
FIG. 3 shows a flow diagram for performing an ultrasound scan according to another embodiment of the invention.

Referring to FIG. 3 showing a flow diagram for performing an ultrasound scan according to another embodiment of the invention. Initially the control unit 6 receives 611 position data from the sensor 5. The sensor 5 being a 2D and/or a 3D camera. The position data comprising information regarding a position and an orientation of a body part of a patient. Based on the received position data, the control unit 6 determines 612 a target area on the body part. The target area may be an area comprising points of interest, e.g. one or more joints of a hand or a foot. The target area may be determined by executing a vision algorithm on the received position data. The control unit 6 determines 613 a first movement instruction for the positioning device 4 for moving the ultrasound probe 31 wherein the first movement instruction is for moving the ultrasound probe within the target area to obtain the first ultrasound image of the body part. The first movement instruction comprising a plurality of first positions and a plurality of first orientations defining a scanning path for moving the positioning device 4. The first movement instruction further comprising a control signal for the ultrasound probe 31 for acquiring the plurality of first ultrasound images with a first level of detail. The first movement instruction may instruct the positioning device to continuously move the ultrasound probe along the scanning path and to achieve the first ultrasound images in a sweeping manner. The first ultrasound images may then be a sequence of first ultrasound images obtained along the scanning path. The plurality of first positions and the plurality of first orientations defines a scanning path within the target area, thus allowing the ultrasound probe to scan the body part at the plurality of first positions and the plurality of first orientations within the target area. The control unit 6 receives 614 from the ultrasound imaging system a plurality of first ultrasound images of the body part. The plurality of first ultrasound images may be received over a wired and/or a wireless connection. The control unit 6 assigns 615 a score to each first ultrasound image of the plurality of received first ultrasound image using a machine learning data architecture trained to evaluate an ultrasound image of the body part. The score assigned may be indicative of a picture quality and/or whether an anatomical feature is correctly captured. The control unit 6 sorts 616 the plurality of first ultrasound images into a first group or a second group. The sorting may be based on whether if the score assigned a first ultrasound image of the plurality of first ultrasound images is under a quality threshold the first ultrasound image is sorted into the second group, wherein if the score assigned the first ultrasound image is over the quality threshold the first ultrasound image is sorted into the first group. The one or more first ultrasound images sorted into the second group may simple be discarded as not useful for further purposes. The control unit 6 determines 617 one or more acquiring positions and one or more acquiring orientations corresponding to a position and/or an orientation of the ultrasound probe 31 and/or the positioning device 4 when the one or more first ultrasound image sorted in the first group was obtained. The control unit 6 generates 618 the second movement instruction comprising the one or more acquiring positions and the one or more acquiring orientations for the positioning device 4 for moving the ultrasound probe 41 to obtain one or more second ultrasound images of the body part. The second movement instruction further comprising a control signal for the ultrasound probe for acquiring the one or more ultrasound images with a second level of detail, wherein the second level of detail is higher than the first level of detail. The control unit 6 receives 619 from the ultrasound imaging system one or more second ultrasound image of the body part. The con-trot unit 6 assigns 620 a score to each of the one or more second ultrasound images using the machine learning data architecture trained to evaluate an ultrasound image of the body part. The control unit 6 sorts 621 the one or more second ultrasound images into a third group or a fourth group based on the second score assigned. For example, if the score assigned a second ultrasound image is under a quality threshold the second ultrasound image is sorted into the fourth group, wherein if the score assigned the second ultrasound image is over the quality threshold the second ultrasound image is sorted into the third group. The control unit 6 repeats 622 the ultrasound scan on the body part, if the third group is empty after sorting the one or more second ultrasound image. if the second ultrasound image is sorted into the third group, the control unit 6 generates 623 an ultrasound control signal for the ultrasound imaging system to obtain a third ultrasound, wherein the third ultrasound image comprises a third level of detail, and wherein the third level of detail is higher than the first level of detail and the second level of detail.

The different steps carried out by the control unit 6 may be carried out simultaneously or in sequence. For example, the control unit 6 may assign scores to ultrasound image while simultaneously sorting them into groups. The control unit 6 may receive ultrasound images while simultaneously evaluating the received ultrasound images.

Figure 4:
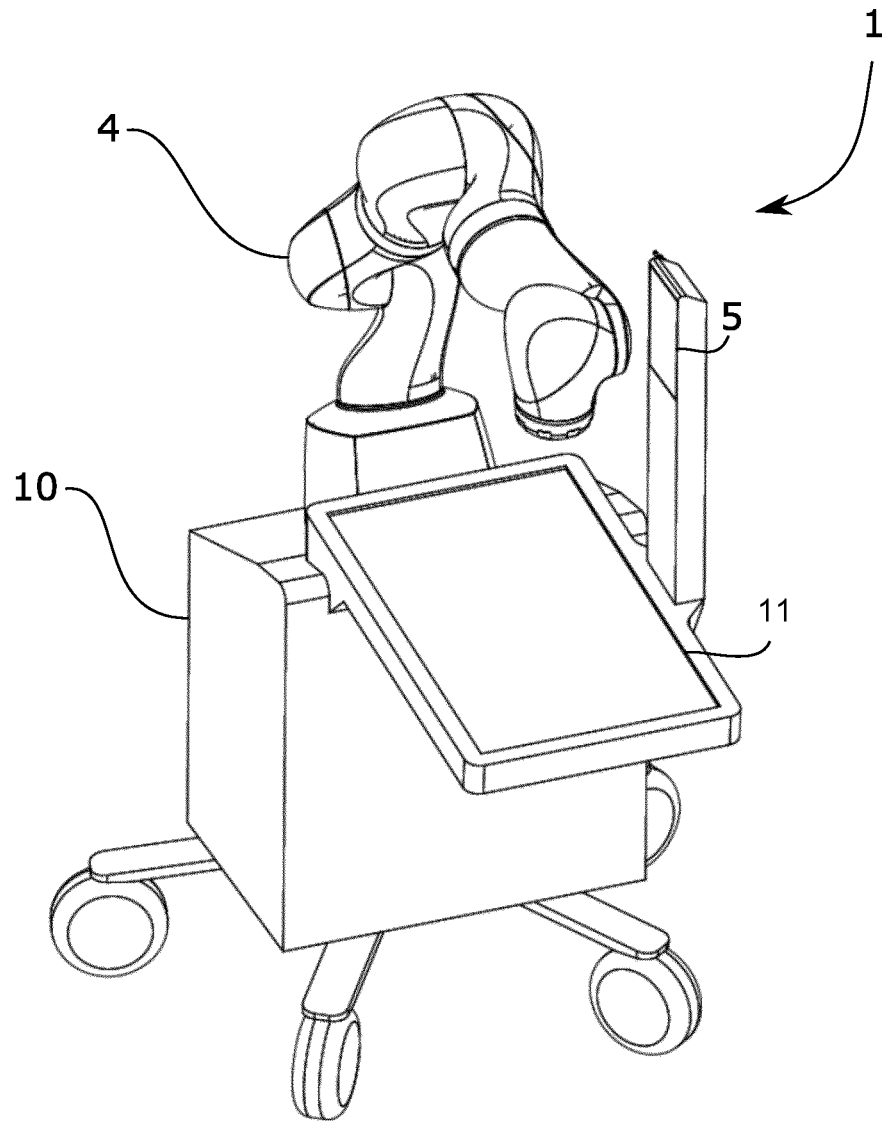
FIG. 4 shows a schematic perspective view of an embodiment of a robotic system according to an embodiment of the invention.

Referring to FIG. 4 showing a schematic perspective view of an embodiment of a robotic system 1 according to an embodiment of the invention. The robotic system 1 being configured for performing an ultrasound scan on a body part of a patient. To carry out the ultrasound scan the robotic system 1 is provided with an articulated arm 4. The articulated arm 4 is configured to hold an ultrasound probe and move the ultrasound probe to obtain the ultrasound scan of the body part.

A control unit, not shown, is housed within a system housing 10. The control unit is communicatively connected to the articulated arm 4, thus allowing the control unit to transmit movement instructions to the articulated arm 4. The control unit is further communicatively connected to a sensor 5 to receive position data from the sensor 5. The sensor is a 3D camera configured to obtain image data on the body part.

The robotic system 1 further comprises a support surface 11 on which a body part of a patient undergoing the ultrasound scan can rest.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

What is claimed is:

1. A robotic system for performing an ultrasound scan on a body part of a patient using an ultrasound imaging system comprising an ultrasound probe, the robotic system comprising:

a positioning device holding and moving the ultrasound probe to obtain the ultrasound scan of the body part, a sensor configured to obtain position data on the body part, and a control unit operatively connected to the ultrasound probe and sensor, wherein the control unit is configured to:

receive position data from the sensor, generate, based on the received position data, a first movement instruction for the positioning device for moving the ultrasound probe to obtain a plurality of first ultrasound images of the body part at a plurality of first positions, receive from the ultrasound imaging system the plurality of first ultrasound images of the body part, evaluate the received plurality of first ultrasound images using a machine learning data architecture trained to evaluate ultrasound images of the body part, wherein the evaluation of the plurality of first ultrasound images comprises determining an image quality of the plurality of first ultrasound images, and generate, based on the evaluation of the plurality of first ultrasound images, second movement instructions for the positioning device for moving the ultrasound probe to a position at which at least one of the plurality of first ultrasound images were obtained to obtain a second ultrasound image of the body part at that position, wherein the second movement instructions are for moving the ultrasound probe to the position of the plurality of first positions having a highest determined image quality of the plurality of first ultrasound images.

2. A robotic system according to claim 1, wherein the control unit is further configured to:

determine, based on the received position data, a target area on the body part, and wherein the first movement instruction is for moving the ultrasound probe within the target area to obtain the plurality of first ultrasound images of the body part.

3. A robotic system according to claim 1, wherein the control unit is further configured to:

assign a first score to the plurality of first ultrasound images using the machine learning data architecture trained to evaluate ultrasound images of the body part.

4. A robotic system according to claim 3, wherein the control unit is further configured to:

based on the first score, sort the first plurality of ultrasound images into a first group or a second group.

5. A robotic system according to claim 4, wherein the second movement instructions for the positioning device for moving the ultrasound probe to obtain the second ultrasound image of the body part are generated based on the plurality of first ultrasound images being sorted into the first group, and wherein the second movement instructions comprise one or more of a first acquiring position or a first acquiring orientation of the first plurality of ultrasound images.

6. A robotic system according to claim 1, wherein the control unit control unit is further configured to:

receive from the ultrasound imaging system the second ultrasound image of the body part.

7. A robotic system according to claim 6, wherein the plurality of first ultrasound images comprises a first level of detail, and wherein the second ultrasound image comprises a second level of detail, and wherein the second level of detail is higher than the first level of detail.

8. A robotic system according to claim 7, wherein the control unit is further configured to:

assign a second score to the second ultrasound image using the machine learning data architecture trained to evaluate ultrasound images of the body part.

9. A robotic system according to claim 8, wherein the control unit is further configured to:

based on the second score, sort the second ultrasound image into a third group or a fourth group.

10. A robotic system according to claim 9, wherein the control unit is further configured to:

if the second ultrasound image is sorted into the third group, generate an ultrasound control signal for the ultrasound imaging system to obtain a third ultrasound image, wherein the third ultrasound image comprises a third level of detail, and wherein the third level of detail is higher than the first level of detail and the second level of detail.

11. A robotic system according to claim 1, wherein the first movement instruction for the positioning device for moving the ultrasound probe is a sweeping ultrasound scan along a scanning path, wherein the ultrasound probe is continuously moving.

12. A robotic system for performing an ultrasound scan on a body part of a patient using an ultrasound imaging system comprising an ultrasound probe, the robotic system comprising:

a positioning device holding and moving the ultrasound probe to obtain the ultrasound scan of the body part, a sensor configured to obtain position data on the body part, and a control unit operatively connected to the ultrasound probe and sensor, wherein the control unit is configured to:

receive position data from the sensor, generate, based on the received position data, a first movement instruction for the positioning device for moving the ultrasound probe to obtain a plurality of first ultrasound images of the body part at a plurality of first positions, receive from the ultrasound imaging system the plurality of first ultrasound images of the body part, evaluate the received plurality of first ultrasound images using a machine learning data architecture trained to evaluate ultrasound images of the body part, wherein the evaluation of the plurality of first ultrasound images comprises determining an image quality of the plurality of first ultrasound images, and generate, based on the evaluation of the plurality of first ultrasound images, second movement instructions for the positioning device for moving the ultrasound probe to a position at which at least one of the plurality of first ultrasound images were obtained to obtain a second ultrasound image of the body part at that position, wherein the second movement instructions are for moving the ultrasound probe to a position of the plurality of first positions where the determined image quality of a first ultrasound image of the plurality of first ultrasound images meets a required image quality threshold.

13. A robotic system according to claim 1, wherein the plurality of first ultrasound images is obtained with a first ultrasound scanning mode, and the second ultrasound image is obtained with a second ultrasound scanning mode, wherein the first ultrasound scanning mode and second ultrasound scanning mode are different modes.

14. A robotic system for performing an ultrasound scan on a body part of a patient using an ultrasound imaging system comprising an ultrasound probe, the robotic system comprising:

a positioning device holding and moving the ultrasound probe to obtain the ultrasound scan of the body part, a sensor configured to obtain position data on the body part, and a control unit operatively connected to the ultrasound probe and sensor, wherein the control unit is configured to:

receive position data from the sensor, generate, based on the received position data, a first movement instruction for the positioning device for moving the ultrasound probe to obtain a plurality of first ultrasound images of the body part at a plurality of first positions, receive from the ultrasound imaging system the plurality of first ultrasound images of the body part, evaluate the received plurality of first ultrasound images using a machine learning data architecture trained to evaluate ultrasound images of the body part, and generate, based on the evaluation of the plurality of first ultrasound images, second movement instructions for the positioning device for moving the ultrasound probe to a position at which at least one of the plurality of first ultrasound images were obtained to obtain a second ultrasound image of the body part at that position, wherein the plurality of first ultrasound images is obtained with a b-mode ultrasound scan, and the second ultrasound image is obtained with a Doppler ultrasound scan.

* * * * *